(12) United States Patent
Weiland et al.

(10) Patent No.: US 6,376,430 B1
(45) Date of Patent: Apr. 23, 2002

(54) ENHANCEMENT OF SEED YIELD OF SOYBEANS BY A SUBSTITUTED BENZOYL UREA

(75) Inventors: Robert T. Weiland, Cheshire, CT (US); John G. Connell, Bloomington, IN (US)

(73) Assignee: Uniroyal Chemical Company, Inc., Middlebury, CT (US)

( * ) Notice: Subject to any disclaimer, the term of this patent is extended or adjusted under 35 U.S.C. 154(b) by 0 days.

(21) Appl. No.: 09/486,903
(22) PCT Filed: Sep. 18, 1998
(86) PCT No.: PCT/US98/19624
§ 371 Date: Mar. 3, 2000
§ 102(e) Date: Mar. 3, 2000
(87) PCT Pub. No.: WO99/16316
PCT Pub. Date: Apr. 8, 1999

Related U.S. Application Data
(60) Provisional application No. 60/060,501, filed on Sep. 30, 1997.

(51) Int. Cl.$^7$ .......................... A01N 47/34; A01H 1/00; A01H 5/00
(52) U.S. Cl. ...................... 504/328; 504/329; 800/279; 800/312
(58) Field of Search .................. 504/328, 329; 800/279.312

(56) References Cited

PUBLICATIONS

White, P.E., Effects Of Bendiocarb and Diflubenzuron on Mushroom Cropping, Ann. Appl. Biol., 108, 11–20, 1986.*
Da Silva, evaluation of the Efficiency of Biological and Physiological insecticides in the control of the Velvetbean Caterpillar in Soybean, Rev. Cent. Cienc. Rurais (Univ. Fed. St. Maria), 1986, 16(2), 151–160.*
Von Schaik, P.H.,Probst, A.H., Effects of Some Environmental Factors on Flower Production and Reproductive Efficiency in Soybeans, Agronomy Journal, (1958), pp. 192–197, vol. 50.
Hicks, D.R., Pendleton, J.W., & Scott, W.O., Response of Soybeans to TIBA (2,3,5–Triiodobenzoic Acid) And High Fertility Levels, Crop Science, (1967), pp. 397–398, vol. 7.
Burton, J.C., Curley, R.L., Influence of Triiodobenzoic Acid on Growth, Nodulation and Yields of Inoculated Soybeans, Agronomy Journal, (1966), pp. 406–408, vol. 58.
Bauer, M.E., Sherbeck, T.G., & Ohlrogge, A.J., Effects of Rate, Time, and Method of Application of TIBA on Soybean Production, Agronomy Journal, (1969), pp. 604–606, vol. 61.
Fehr, W.R., Caviness, C.E., Stages of Soybean Development, Special Report, (1977), pp. 3–11, vol. 80, Cooperative Extension Service, Iowa State University, Ames, Iowa.

\* cited by examiner

*Primary Examiner*—Jezia Riley
(74) *Attorney, Agent, or Firm*—Daniel Reitenbach

(57) ABSTRACT

A method is disclosed for increasing yield in soybeams by applying, in the absence of insect pressure on the crop, an amount effective for increasing seed pod formation of an active amount of a substituted benzoyl urea represented by structural formula (I).

10 Claims, No Drawings

ENHANCEMENT OF SEED YIELD OF SOYBEANS BY A SUBSTITUTED BENZOYL UREA

This appln is a 371 of PCT/US98/19624 filed Sep. 18, 1998 which claims benefit of No. 60/060,501 filed Sep. 30, 1997.

BACKGROUND OF THE INVENTION

Field of the Invention

The present invention is directed to a method of increasing soybean (determined as well as indeterminate soybeans) yield by the application of a benzoyl urea of Structure (I). Most preferred method is directed to a narrow application window of reproductive indeterminate soybeans in which the application of an insect growth regulator, such as Structure (I), can enhance the seed yield. The increase in yield is likely ubiquitous with other leguminous plants, such as peanuts, lima beans and navy beans, and even cotton. It appears to be a consequence of increased pod numbers on the plant which consequently gives increased seed yield, since the seeds are no smaller in size/weight.

SUMMARY OF THE INVENTION

A method for increasing yield in soybeans by applying, in the absence of insect pressure on the crop, an amount effective for increasing seed pod formation of an active amount of a substituted benzoyl urea represented by structural formula I:

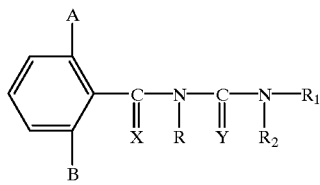
(I)

where A is a hydrogen atom, a halogen atom, a methyl group or a methoxy group,

B also represents a hydrogen atom, a halogen atom, a methyl group or a methoxy group, X and Y each represent an oxygen atom or a sulfur atom, R is a hydrogen atom, an alkyl group, a hydroxy group, an alkoxy group, an alkoxymethyl group, an acyl group or an alkoxycarbonyl group, $R_1$ is a hydrogen atom, any molecule or group of molecules containing at least one carbon atom, preferably, an alkyl group unsubstituted or substituted with halogen, with alkoxy, with alkylthio or with cyano, a 1-cycloalkenyl group, a benzyl group unsubstituted or substituted with halogen, a hydroxy group, an alkoxy group, an acyl group, an alkoxycarbonyl group, an alkoxythiocarbonyl group, an alkylsulfonyl group or a phenylsulfonyl group, while furthermore R and $R_1$ together with the group:

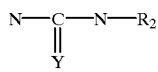

indicated in the above formula may form a ring system, and $R_2$ represents a substituted or non-substituted phenyl group or a pyridyl group unsubstituted or substituted with halogen, with nitrocyano or with halogenated alkyl, wherein said ring system is represented by any of the following formulae:

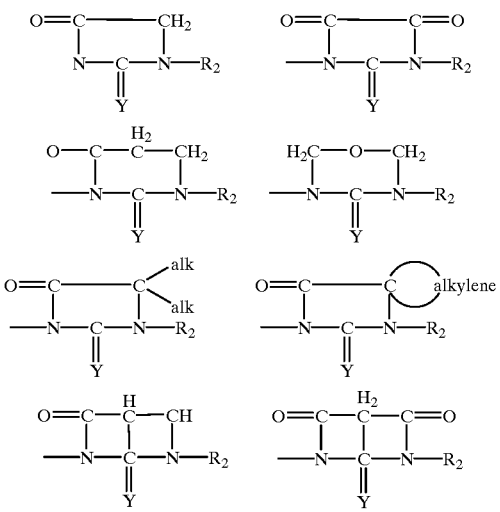

wherein the formulae Y and $R_2$ have the aforementioned meanings, alk is a $C_1$ to $C_{20}$ alkyl group and $C_1$ to $C_{20}$ alkylene is a bivalent saturated alkylene group, if $R_2$ is a substituted phenyl group, the phenyl group contains at least one substituent chosen from the group consisting of:

(a) 1–3 halogen atoms, (b) 1–2 $C_1$ to $C_{20}$ alkyl groups, unsubstituted or substituted with halogen, hydroxy, $C_1$ to $C_{20}$ alkoxy, $C_1$ to $C_{20}$ alkylthio, $C_1$ to $C_{20}$ dialkyl amino, alkylsulphonyl and phenyl, (c) tri- or tetramethylene, (d) a $C_1$ to $C_{20}$ cycloalkyl group, unsubstituted or substituted with halogen or cyano, (e) 1–2 nitro groups or cyano groups or alkoxy groups, (f) a dioxymethylene or dioxyethylene group, (g) an acyl group, unsubstituted or substituted with halogen, (h) an alkyl sulfonyl, phenyl sulfonyl, alkylthio, phenylthio or phenoxy group, unsubstituted or substituted with halogen, (i) a sulfonic group, which may alkylated, and (j) a phenyl group, unsubstituted or substituted with halogen, nitro, cyano, and halogenated alkyl, wherein all alkyl references, unless otherwise noted are C1 to C20.

A more preferred subgenus of structural formula (I) is represented by structural formula (II):

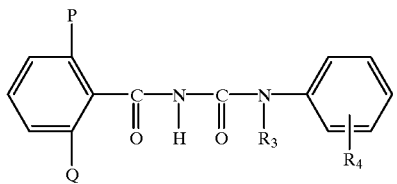
(II)

P and Q may be equal or different and each represent a chlorine atom, a fluorine atom or a methyl group, $R_3$ represents a hydrogen atom, an alkyl group, a benzyl group, an acyl group or an alkoxycarbonyl group, R₄ represents from 0–3 substituents selected from the group comprising from 1 to 3 halogen atoms, an alkyl group which contains from 1 to 15 carbon atoms and may be substituted with one or more halogen atoms or with a phenyl group, a cycloalkyl group unsubstituted or substituted with at least one halogen atom a nitro group, a cyano group, a phenyl group, a thiophenyl group, a benzoyl group, a thioalkyl group and an alkylsulfonyl group.

A still more preferred set of substituted benzoyl urea is of the formulae:

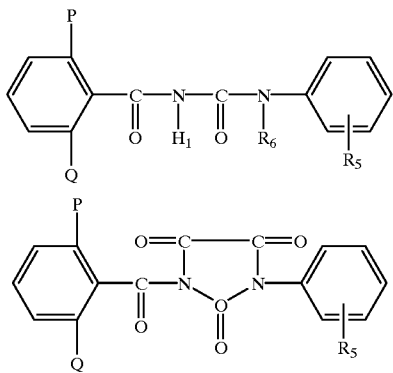

where P and Q may be equal or different and each represent a chlorine atom, a fluorine atom or a methyl group, R₆ is a hydrogen atom or a lower alkyl group and R₅ represents 1–3 substituents selected from the group comprising 1–3 halogen atoms, an alkyl group which contains from 1 to 15 carbon atoms unsubstituted or substituted with at least one halogen atom, and a cycloalkyl group unsubstituted or substituted with at least one halogen atom, preferably R₅ represents one or two substituents in the position 3 or the position 4 or the positions 3 and 4 of the phenyl group.

Also preferred substituted benzoyl urea of the formulae:

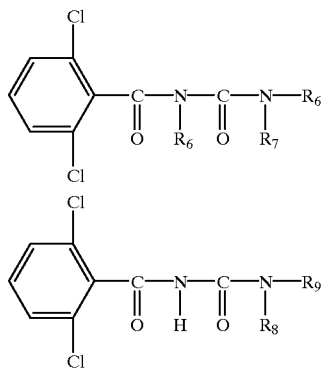

where R₆ is a hydrogen atom or a lower alkyl group, R₇ represents a unsubstituted or substituted phenyl group, R₉ is a hydrogen atom or a methyl group, R₈ represents a phenyl group unsubstituted or substituted with 1–3 halogen atoms, an alkyl group, cyclo-alkyl group, nitro group, tetramethylene group, methylenedioxy group or a methylsulfonyl group.

Preferred benzoyl ureas include:
a substituted benzoyl urea selected from the group consisting of
N-(2,6-dichlorobenzoyl)-N'-(3,4-dichlorophenyl)urea,
N-(2,6-difluorobenzoyl)-N'-(3,4-dichlorophenyl)urea,
N-(2,6-dimethylbenzoyl)-N'-(3,4-dichlorophenyl)urea,
N-(2,6-dichlorobenzoyl)-N'-(4-chlorophenyl)urea,
N-(2,6-dimethylbenzoyl)-N'-(4-chlorophenyl)urea,
N-(2,6-dichlorobenzoyl)-N'-(2,4-dichlorophenyl)urea,
N-(2,6-dichlorobenzoyl)-N'-(4-cyclopropylphenyl)urea,
N-(2,6-dichlorobenzoyl)-N'-(3-chloro-4-iodophenyl)urea,
N-(2,6-dichlorobenzoyl)-N'-(3-chloro-4-bromophenyl)urea,
N-(2,6-dichlorobenzoyl)-N'-(4-isopropylphenyl)urea,
N-(2,6-dichlorobenzoyl)-N'-(3,4-dibromophenyl)urea,
N-(2,6-dichlorobenzoyl)-N'-(4-fluorophenyl)urea,
N-(2,6-dichlorobenzoyl)-N'-(3-trifluoromethylphenyl)urea,
N-(2,6-dichlorobenzoyl)-N'-(4-n-butylphenyl)urea,
N-(2,6-dichlorobenzoyl)-N'-(3-chloro-4-methylsulfonylphenyl)urea,
N-(2,6-dichlorobenzoyl)-N'-(4-t-butylphenyl)urea,
N-(2,6-dichlorobenzoyl)-N'-(3,4-difluorophenyl)urea,
N-(2,6-dichlorobenzoyl)-N'-(2,4-difluorophenyl)urea,
N-(2,6-dichlorobenzoyl)-N'-(4-bromophenyl)urea,
N-(2,6-dichlorobenzoyl)-N'-(2,5-difluoro-4-bromophenyl)urea,
N-(2,6-dichlorobenzoyl)-N'-(4-iodophenyl)urea,
N-(2,6-dichlorobenzoyl)-N'-(3-fluoro-4-chlorophenyl)urea,
N-(2,6-dichlorobenzoyl)-N'-(4-phenylphenyl)urea,
N-(2,6-dichlorobenzoyl)-N'-(4-cyanophenyl)urea,
N-(2,6-dichlorobenzoyl)-N'-(3-fluoro-4-bromophenyl)urea,
N-(2,6-dichlorobenzoyl)-N'-(3-fluoro-4-iodophenyl)urea,
N-(2,6-dichlorobenzoyl)-N'-(2-fluoro-4-iodophenyl)urea,
N-(2,6-dichlorobenzoyl)-N'-(4-n-propylphenyl)urea,
N-(2,6-dichlorobenzoyl)-N'-(4-trifluoromethylphenyl)urea,
N-(2,6-dichlorobenzoyl)-N'-(3-cyclopropylphenyl)urea,
N-(2,6-dichlorobenzoyl)-N'-(2-methyl-4-chlorophenyl)urea,
N-(2,6-dichlorobenzoyl)-N'-(4-sec-butylphenyl)urea,
N-(2,6-dichlorobenzoyl)-N'-(4-iso-butylphenyl)urea,
N-(2,6-dichlorobenzoyl)-N'-(4-ethylphenyl)urea,
N-(2,6-dichlorobenzoyl)-N'-(4-n-dodecylphenyl)urea,
N-(2,6-dichlorobenzoyl)-N'-4-benzylphenyl)urea,
N-(2,6-dibromobenzoyl)-N'-(3,4-dichlorophenyl)urea,
N-(2,6-dichlorobenzoyl)-N'-(methyl)-N'-(3,4-dichlorophenyl)urea,
N-(2,6-dichlorobenzoyl)-N'-(ethyl)-N'-(3,4-dichlorophenyl)urea,
N-(2,6-dichlorobenzoyl)-N'-(methyl)-N'-(4-t-butylphenyl)urea,
N-(2,6-dichlorobenzoyl)-N'-(methyl)-(4-bromophenyl)urea,
N-(2,6-dichlorobenzoyl)-N'-(ethyl)-N'-(4-bromophenyl)urea,
N-(2,6-dichlorobenzoyl)-N'-(ethyl)-N'-(4-isopropylphenyl)urea,
N-(2,6-dichlorobenzoyl)-N'-(ethyl)-N'-(4-n-butylphenyl)urea,
N-(2,6-dichlorobenzoyl)-N'-(methyl)-N'-(4-chlorophenyl)urea,
N-(2,6-dichlorobenzoyl)-N'-(ethyl)-N'-(4-chlorophenyl)urea,
N-(2,6-dichlorobenzoyl)-N'-(ethyl)-N'-(4-t-butylphenyl)urea,
N-(2,6-dichlorobenzoyl)-N'-(methyl)-N'-(4-nitrophenyl)urea,
3-(2,6-dichlorobenzoyl)-1-(4-chlorophenyl)-parabanic acid
N-(2,6-dichlorobenzoyl)-N'-(2,4,5-trichlorophenyl)urea,
N-(2,6-dichlorobenzoyl)-N'-(phenyl)urea,
N-(2,6-dichlorobenzoyl)-N'-(4-nitrophenyl)urea,
N-(2,6-difluorobenzoyl)-N'-(4-trifluoromethylphenyl)urea,
N-(2,6-difluorobenzoyl)-N'-(4-n-butylphenyl)urea,
N-(2,6-difluorobenzoyl)-N'-(4-t-butylphenyl)urea, N-(2,6-difluorobenzoyl)-N'-(4-isopropylphenyl)urea,
N-(2,6-difluorobenzoyl)-N'-(3-fluoro-4-iodobenzyl)urea,
N-(2,6-difluorobenzoyl)-N'-(3-fluoro-4-chlorophenyl)urea,
N-(2,6-difluorobenzoyl)-N'-(3-trifluoromethylphenyl)urea,
N-(2,6-difluorobenzoyl)-N'-(4-isobutylphenyl)-N'-(methyl)urea,
N-(2,6-difluorobenzoyl)-N'-(4-chlorophenyl)urea,
N-(2,6-difluorobenzoyl)-N'-(4-bromophenyl)urea,
N-(2,6-difluorobenzoyl)-N'-(4-fluorophenyl)urea,
N-(2,6-difluorobenzoyl)-N'-(4-thiomethylphenyl)urea,
N-(2,6-difluorobenzoyl)-N'-(methyl)-(4-chlorophenyl)urea, and
N-(2,6-difluorobenzoyl)-N'-(methoxymethyl)-N'-(3,4-dichlorophenyl)urea.

Also useful may be: N-(((3-chloro-4-(1,1,2-trifluoro-2-trifluoromethoxy)ethoxy)phenyl)amino)carbonyl)-2,6-difluorobenzamide; 1-[α-(4-chloro-α-cyclopropylbenzylideneamino-oxy)-p-tolyl]-3-(2,6-difluorobenzoyl)urea; 1-[3,5-dichloro-4-(3-chloro-5-trifluoromethyl-2-pyridyloxy)phenyl]-3-(2,6-difluorobenzoyl)urea; 1-[4-(2-chloro-α,α,α-trifluoro-p-tolyloxy)-2-fluorophenyl]-3-(2,6- difluorobenzoyl)urea; 1-(3,5-dichloro-2,4-difluorophenyl)-3-(2,6-difluorobenzoyl)urea; 1-(2-chlorobenzoyl)-3-(4-trifluoromethoxyphenyl)urea; 1-[3,5-dichloro-4-(1,1,2,2-tetrafluoroethoxy)phenyl]-3-(2,6-difluorobenzoyl)urea; and N-[2,5-dichloro-4-(1,1,2,3,3,3-hexafluoropropoxy)-phenylaminocarbonyl]-2,6-difluorobenzamide.

PREFERRED EMBODIMENT

The active ingredient of Structure I may be applied in any effective rate from 0.0001 kg/ha to 10 kg/ha, preferably 0.001 to 0.1 kg/ha, more preferably 0.01 to 0.06 and most preferably 0.02 to 0.09 kg./ha. Each of the species of formula (I) requires reasonable experimentation to determine the optimal rate.

Structure I represented by it most effective compound, Diflubenzuron, is an insect growth regulator which is active on many foliar feeding insects which need to be controlled in southern U.S. soybeans. These soybeans exhibit determinate growth which is typified by little growth in height after flowering begins, in contrast to indeterminate growth exhibited by northern U.S. types. The latter generally have achieved less than half their final height when flowering begins. In controlling insects in the South, it has previously been determined that use of Diflubenzuron can increase soybean seed yields, even when target pest infestations are lower than the economically damaging threshold. This increase has been shown when Diflubenzuron was applied between the full bloom and beginning seed reproductive stages. When Diflubenzuron was applied to indeterminate types of the North, which typically have little or no pressure from foliar feeding insects, the yield enhancement period was unexpectedly narrowed to the reproductive period from beginning pod to prior to full pod.

DETAILED DESCRIPTION OF THE INVENTION

Structural formulae I and II, represented by Diflubenzuron, belongs to the substituted 1-benzoyl-3-phenylurea family of pesticides. The compounds act on insects by interfering with the production/deposition of chitin, one of the main components of the insect exoskeleton.

After treatment with, Diflubenzuron, larvae have difficulties with the molting process. This results in an inability to successfully cast off the old exoskeleton and leads to the eventual death of the larva. The mode of action of Diflubenzuron also gives rise to trans-ovarial effects by interfering with chitin deposition of the developing larva in the egg. Diflubenzuron exhibits long residual on plant tissue, but readily dissipates in soil or aqueous media. The compound is not considered systemic in the plant, therefore sucking insects are not usually affected.

Diflubenzuron provides control of a number of important pests in a variety of fruits, field crops, pasture and turf, and horticulture products. Of particular interest in this invention is soybeans. Diflubenzuron is labeled to control soybean pests which include velvetbean caterpillar (*Anticarsia gemmatalis*), Mexican bean beetle (*Epilachna varivestis*), green cloverworm (*Plathypena scrabra*), beet armyworm (*Spodoptera exigua*), and fall armyworm (*Spodoptera frugiperda*). These insects can be considered economically damaging pests in soybeans grown in southern U.S.; green cloverworm can occasionally cause significant damage in northern U.S. This use for insects is known but this method involves the application of Diflubenzuron, in the absence of substantial insect presence or "insecticidal pressure", on the crop to increase soybean seed yields.

Application Rates and Conditions

The application of Diflubenzuron to soybeans can be made up to 21 days from harvest. A total of 0.069 kg ai/ha/year (0.062 lb ai/acre/year) can be applied. Typically soybeans are treated for control of foliar feeding insects during the plant's reproductive period up to the point where damage will no longer limit final seed yield. The reproductive period can be segmented into different stages. Fehr and Caviness (1981) describe 8 "R" stages. They are R1, or beginning bloom; R2, Ror full bloom; R3, Ror beginning pod; R4, Ror full pod; R5, Ror beginning seed; R6, Ror full seed; R7, Ror beginning maturity; and R8, Ror full maturity. These growth stages are further described in Table 1.

The growth stages of Fehr and Caviness (1981) apply to both the determinate soybeans typically grown in the southern U.S., and the indeterminate soybeans typically grown in the northern U.S., except R1 and R2 generally occur simultaneously in determinate varieties. There are major differences in plant development between indeterminate and determinate varieties. Indeterminates generally have grown less than half their final height when flowering begins, and they grow taller and produce branches while flowering, pod development and seed development are occurring. Pod and seed development on the lower portion of this plant are more advanced than on the top portion. The top of the indeterminate plant usually has smaller leaves than those lower on the plant, and additionally, there are few pods at the terminal (Fehr and Caviness, 1981).

Determinate varieties usually grow very little in height after flowering begins. Flowering occurs approximately the same time in the top and bottom of the plant; and thus, pod and seed development are about the same throughout the plant. The determinate plant has a terminal leaf on the main stem that is about the same size as lower ones on the plant. The terminal node on the main stem usually bears a long flowering stalk, or raceme, which has a number of pods (Fehr and Caviness, 1981). It should be noted that up to 80% of flowers formed on a soybean plant can be aborted as a flower or pod (van Schaik and Probst, 1958), regardless if determinate or indeterminate. These authors also cite papers which describe other legumes (e.g. peanut, lima beans, white pea beans) and cotton as having a high number of flowers and/or fruiting structures aborting.

In this invention, Diflubenzuron is typically sprayed during the period from R2 through R5 for controlling foliar feeding insects. In the States of Mississippi, Florida, Tennessee, Illinois, Arkansas, Louisiana, and Texas results have been compiled where one or two field applications of Diflubenzuron at 0.034 kg ai/ha (0.031 lb ai/acre) were applied to control insects on the determinate soybeans planted. A fungicide, Benomyl, methyl-1-(butylcarbamoyl)-2-benzamidazolecarbamate [CAS 17804-35-2], available as BENLATE™ from DuPont deNemour, Wilmington, Del., was also applied alone or in combination with Diflubenzuron for fungal pathogen control. This 29 site data base (Table 2) shows Diflubenzuron alone, Benomyl (methyl-1-(butylcarbamoyl)-2-benzamidazolecarbamate) alone, and Diflubenzuron+Benoymyl (methyl-1-(butylcarbamoyl)-2-benzamidazolecarbamate) gave respective 2.8, 3.7 and 6.3 bushels/acre increases over the untreated control. It was observed that Diflubenzuron surprisingly gave yield increases even though insects were not consistently present at yield limiting levels across the trials. The benefit of using Diflubenzuron or Benomyl (methyl-1-(butylcarbamoyl)-2-benzamidazolecarbamate) alone would appear to be additive, as seen in the combination results.

Since significant insect pressure did not need to be present in southern determinate soybeans, this potential yield increase with Diflubenzuron was additionally field examined on northern indeterminate soybean varieties, alone and in combination with Benomyl (methyl-1-(butylcarbamoyl)-2-benzamidazolecarbamate. Applications of Diflubenzuron at 0.034 kg/ha (0.031 lb ai/acre) at 25 sites across Indiana, Illinois, Iowa, Kentucky, and Michigan on many commercial varieties ranged from the R2 through the R5 growth stage. Diflubenzuron alone increased seed yield by 155 kg/ha (2.3 bushels per acre) and the combination with Benomyl (methyl-1-(butylcarbamoyl)-2-benzamidazolecarbamate) increased yield by an additional 0.8 bushels (Table 3). A general assessment across the reproductive stages indicated that any increase was predominately due to application at R3 or R3.5 (approximately ½ the plants were at either R3 or R4) (Table 3). Diflubenzuron alone gave a 376 kg/ha (5.6 bu/acre) increase over the untreated control; the addition of Benomyl (methyl-1-(butylcarbamoyl)-2-benzamidazolecarbamate) only conferred another 0.5 bushel increase. There were no reported foliar feeding insect infestations of significance in any of the trials. It is not surprising that Benomyl (methyl-1-(butylcarbamoyl)-2-benzamidazolecarbamate) did not confer additional yield in contract to Diflubenzuron alone since fungal pathogens are not a major problem in northern states of the U.S. However, this treatment additionally supports the results of Diflubenzuron sprayed alone for increasing seed yields in indeterminate yields.

If soybean seed yields are increased, this can be accomplished by: a) increased seed size, b) more seed per plant, or c) combination of both of these. In the case of "b", additional pods or an increase in number of seed per pod would result in an increase, as long as the size/mass of the seed did not decrease.

Currently there are no commercially available compounds being used to increase soybean seed numbers. One chemistry, 2,3,5-triiodobenzoic acid (TIBA), was mainly investigated prior to 1970 as a seed yield enhancer. It was reported to increase total seed number per plant but often no corresponding increase in seed yield was found because smaller seeds were formed (e.g. Bauer et al., 1969; Burton and Curley, 1966; Hicks et al., 1967). Besides shortening stem internodes, creating a pyramidal or triangular-shaped canopy versus a nearly flat one, reducing leaflet size, and causing a vertical orientation of the upper leaflets, TIBA shortened the seed filling period by several days. The latter observations could influence the carbon fixation pool of the plant and thus negate the potential yield increase, even if there were additional seeds on the plant.

Although total pods per plant were not determined in the trials with Diflubenzuron, determination of seed size showed only about a 2% variation across varieties with no correlation to application time of Diflubenzuron. Preliminary results show indeterminate soybean trials with Diflubenzuron show pod counts from plants are approximately 16% higher on those treated with Diflubenzuron in relation to the untreated control. This is a similar % increase to the increased seed yields found in Table 3. Visual alteration of the soybean plant canopy with Diflubenzuron, contrary to TIBA, has not been noted in any research trial. Thus Diflubenzuron may be more consistent than TIBA in generating soybean seed yield increases since Diflubenzuron is not visually altering the carbon fixation pool of the plant.

The term "an effective amount" is any amount of active ingredient (ai) with a suitable carrier applied in any manner to the soybeans which increase the pod yield and or the total yield compared to controls without the benzoyl ureas listed above.

Formulation of Active Ingredient

A "suitable carrier" for the purposes of this invention, is any solid or liquid which is biologically, chemically, and physically compatible with the compound of formula I.

A suitable carrier useful in the fungicidal compositions of this invention, can be a finely divided or granular organic or inorganic inert material. Useful inert carriers include attapulgate clay, sand, vermiculite, corncobs, activated carbon and mineral silicates such as mica, talc, pyrophyllite and clays.

The suitable carrier can also be a solvent. The compound of formula I is dissolved in a suitable solvent, or mixture of solvents, which acts as the carrier. Useful solvents include acetone, methanol, ispropanol, t-butyl alcohol, cyclohexanone, toluene, xylene, dioxane, dimethylformamide, dimethylsulfoxide, ethylene dichloride, diacetone alcohol, and N-methylpyrrolidone.

The compound of formula I can also be dissolved in a suitable solvent or mixture of solvents, together with a surface active agent, to produce an emulsion. Examples of useful surface active agents can be found, e.g., in *McCutcheon's Detergents and Emulsifiers* (Allured Publishing Corp., Ridgewood, N.J., 1970); U.S. Pat. Nos. 2,514,916; and 2,547,734. The surface active agents can be anionic, non-ionic or cationic.

The suitable carrier can be a dispersant comprising a suitable solvent, a suitable surface active agent, and water. The compound of formula I can be dissolved in the solvent to form a solution and the solution can then be dispersed in the water with the aid of the surface active agent.

The compound of formula I can also be premixed with an inert solid carrier which is added to a surface active agent and water to provide another form of dispersion type carrier.

The composition of this invention can take the form of dust, granules or a paste of a wettable powder. The compound of formula I is admixed with an inert solid carrier to form a solid composition. To form a powder, the solid inert carrier, such as a mineral silicate, is provided in powder form. The solid composition can be made wettable by the addition of a surface active agent.

Finally, the suitable carrier can be an aerosol. To prepare an aerosol composition, the compound of formula I is initially dissolved in a volatile first solvent. The resultant solution is then admixed with a highly volatile solvent, a liquid aerosol carrier. A highly volatile solvent is liquid only under elevated pressure. At ordinary temperatures and at atmospheric pressure, the highly volatile solvent is a gas. The liquid aerosol carrier is a highly volatile solvent but the volatile first solvent is not a highly volatile solvent. The aerosol carrier can itself be pesticidally active. For example, the aerosol carrier can be an insecticide, a herbicide, a bactericide, or the like. Particularly preferred are the compositions of this invention comprising solvents and emulsions.

TABLE 2

Effect of Diflubenzuron 0.035 kg/ha (≧0.031 lb ai/acre), BENLATE ™ 0.56 to 0.84 kg/ha (8 to 12 oz/acre) and their combination on determinate soybean yields in Arkansas, Florida, Illinois, Louisiana, Mississippi, North Carolina, Tennessee, and Texas when applied from R2 through R5 growth stages:

| DIFLUBENZURON | BENOMYL | DIFLUBENZURON + BENOMYL | UNTREATED CONTROL |
|---|---|---|---|
| 2378 kg/ha | 2439 kg/ha | 2614 kg/ha | 2190 kg/ha |

TABLE 3

The effect of Diflubenzuron 0.035 kg/ha (0.031 lb ai/acre) and Diflubenzuron + BENLATE ™ 0.56 kg/ha (8 oz/acre) on indeterminate soybean yields in Indiana, Illinois, and Michigan, when applied R2 through R5 growth stages:

| Growth stage | No. of Sites | Diflubenzuron | Diflubenzuron + Benomyl | Untreated Control |
|---|---|---|---|---|
| R2 to R5 | 25 | 2795 kg/ha | 2849 kg/ha | 2641 kg/ha |
| R2 to R2.5 | 4 | 2903 kg/ha | 2976 kg/ha | 2916 kg/ha |
| R3 to R3.5 | 12 | 3050 kg/ha | 3084 kg/ha | 2674 kg/ha |
| R4 to R5 | 9 | 2412 kg/ha | 2473 kg/ha | 2479 kg/ha |

TABLE 1

Description of soybean reproductive stages

| Stage | Abbrev. Stage Title | Description |
|---|---|---|
| R1 | Beginning bloom | One open flower at any node on the main stem. |
| R2 | Full bloom | Open flower at one of the two uppermost nodes on the main stem with a fully developed leaf. |
| R3 | Beginning pod | Pod 5 mm long at one of the four uppermost nodes on the main stem with a fully developed leaf. |
| R4 | Full pod | Pod 2 cm long at one of the four uppermost nodes on the main stem with a fully developed leaf. |
| R5 | Beginning seed | Seed 3 mm long in a pod at one of the four uppermost nodes on the main stem with a fully developed leaf. |
| R6 | Full seed | Pod containing a green seed that fills the pod cavity at one of the four uppermost nodes on the main stem with a fully developed seed. |
| R7 | Beginning maturity | One normal pod on the main stem that has reached its mature pod color. |
| R8 | Full maturity | Ninety-five percent of the pods that have reached their mature pod color. |

Source of Table 1: Fehr, W.R. and C.E. Caviness. 1981. Stages of soybean development. Special Report 80. 11 pages. Cooperative Extension Service, Iowa State University, Ames

What is claimed is:

1. A method for increasing yield in soybeans by applying, in the absence of insect pressure on the crop, an amount effective for increasing seed pod formation of a substituted benzoyl urea represented by structural formula:

(I)

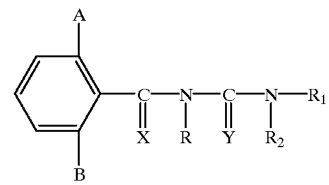

where A is a hydrogen atom, a halogen atom, a methyl group or methoxy group,

B also represents a hydrogen atom, a halogen atom, a methyl group or a methoxy group, X and Y each represent an oxygen atom or a sulfur atom, R is a hydrogen atom, an alkyl group, a hydroxy group, an alkoxy group, an alkoxymethyl group, an acyl group or an alkoxycarbonyl group, $R_1$ is a hydrogen atom, an alkyl group unsubstituted or substituted with halogen, with alkoxy, with alkylthio or with cyano, a 1-cycloalkenyl group, a benzyl group unsubstituted or substituted with halogen, a hydroxy group, an alkoxy group, an acyl group, an alkoxycarbonyl group, an alkoxythiocarbonyl group, an alkylsulfonyl group or a phenylsulfonyl group, while furthermore R and $R_1$ together with the group below may form a ring system 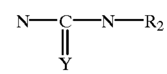 $R_2$ represents a substituted or non-substituted phenyl group or a pyridyl group unsubstituted or substituted with halogen, with nitrocyano or with halogenated alkyl, wherein said ring system is represented by any of the following formulae:

wherein the formulae Y and $R_2$ have the aforementioned meanings, alk is an alkyl group and alkylene is a bivalent saturated alkylene group, if $R_2$ is a substituted phenyl group, the phenyl group contains at least one substituent chosen from the group consisting of:

(a) 1–3 halogen atoms, (b) 1–2 alkyl groups, unsubstituted or substituted with halogen, hydroxy, alkoxy, alkylthio, dialkyl amino, alkysulphonyl and phenyl, (c) tri- or tetramethylene,
(d) a cycloalkyl group, unsubstituted or substituted with halogen or cyano,
(e) 1–2 nitro groups or cyano groups or alkoxy groups,
(f) a dioxymethylene or dioxyethylene group,
(g) an acyl group, unsubstituted or substituted with halogen,
(h) an alkyl sulfonyl, phenyl sulfonyl, alkylthio, phenylthio or phenoxy group, unsubstituted or substituted with halogen,
(i) a sulfonamide group, which may be alkylated, and
(j) a phenyl group, unsubstituted or substituted with halogen, nitro, cyano and halogenated alkyl.

2. A method according to claim 1 wherein the substituted benzoyl urea is represented by structural formula II:

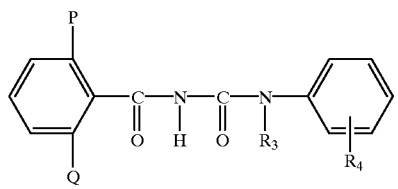

(II)

P and Q may be equal or different and each represent a chlorine atom, a fluorine atom or a methyl group, $R_3$ represents a hydrogen atom, an alkyl group, a benzyl group, an acyl group or an alkoxycarbonyl group, $R_4$ represents from 0–3 substituents selected from the group comprising from 1 to 3 halogen atoms, an alkyl group which contains from 1 to 15 carbon atoms and may be substituted with one or more halogen atoms or with a phenyl group, a cycloalkyl group unsubstituted or substituted with at least one halogen atom, a nitro group, a cyano group, a phenyl group, a thiophenyl group, a benzoyl group, a thioalkyl group and an alkylsulfonyl group.

3. A method according to claim 1 wherein the substituted benzoyl urea is represented by structural formula:

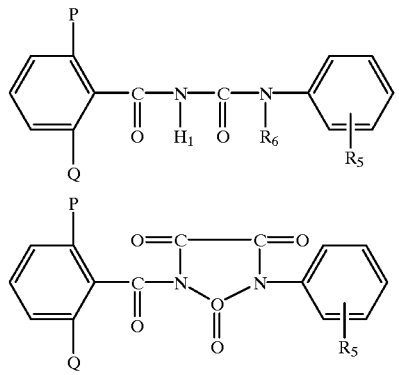

where
P and Q may be equal or different and each represent a chlorine atom, a fluorine atom or a methyl group,
$R_6$ is a hydrogen atom or a lower alkyl group and
$R_5$ represents 1–3 substituents selected from the group consisting of 1–3 halogen atoms, an alkyl group which contains from 1 to 15 carbon atoms unsubstituted or substituted with at least one halogen atom, and a cycloalkyl group unsubstituted or substituted with at least one halogen atom, preferably $R_5$ represents one or two substituents in the position 3 or the position 4 or the positions 3 and 4 of the phenyl group.

4. A method according to claim 1 wherein the substituted benzoyl urea is represented by structural formulae:

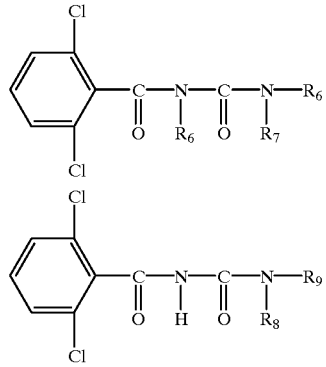

where
$R_6$ is a hydrogen atom or a lower alkyl group, $R_7$ represents a unsubstituted or substituted phenyl group, $R_9$ is a hydrogen atom or a methyl group, $R_8$ represents a phenyl group unsubstituted or substituted with 1–3 halogen atoms, an alkyl group, cyclo-alkyl group, nitro group, tetramethylene group, methylenedioxy group or a methylsulfonyl group.

5. A method for increasing yield in soybeans by applying, in the absence of insect pressure on the crop, an amount effective for increasing seed pod formation of a substituted benzoyl urea selected from the group consisting of:
N-(2,6-dichlorobenzoyl)-N'-(3,4-dichlorophenyl)urea;
N-(2,6-difluorobenzoyl)-N'-(3,4-dichlorophenyl)urea;
N-(2,6-dimethylbenzoyl)-N'-(3,4-dichlorophenyl)urea;
N-(2,6-dichlorobenzoyl)-N'-(4-chlorophenyl)urea;
N-(2,6-dimethylbenzoyl)-N'-(4-chlorophenyl)urea;
N-(2,6-dichlorobenzoyl)-N'-(2,4-dichlorophenyl)urea;
N-(2,6-dichlorobenzoyl)-N'-(4-cyclopropylphenyl)urea;
N-(2,6-dichlorobenzoyl)-N'-(3-chloro-4-iodophenyl)urea;
N-(2,6-dichlorobenzoyl)-N'-(3-chloro-4-bromophenyl)urea;
N-(2,6-dichlorobenzoyl)-N'-(4-isopropylphenyl)urea;
N-(2,6-dichlorobenzoyl)-N'-(3,4-dibromophenyl)urea;
N-(2,6-dichlorobenzoyl)-N'-(4-fluorophenyl)urea;
N-(2,6-dichlorobenzoyl)-N'-(3-trifluoromethylphenyl)urea ;
N-(2,6-dichlorobenzoyl)-N'-(4-n-butylphenyl)urea;
N-(2,6-dichlorobenzoyl)-N'-(3-chloro-4-methylsulfonylphenyl)urea;
N-(2,6-dichlorobenzoyl)-N'-(4-t-butylphenyl)urea;
N-(2,6-dichlorobenzoyl)-N'-(3,4-difluorophenyl)urea;
N-(2,6-dichlorobenzoyl)-N'-(2,4-difluorophenyl)urea;
N-(2,6-dichlorobenzoyl)-N'-(4-bromophenyl)urea;
N-(2,6-dichlorobenzoyl)-N'-(2,5-difluoro-4-bromophenyl)urea;
N-(2,6-dichlorobenzoyl)-N'-(4-iodophenyl)urea;
N-(2,6-dichlorobenzoyl)-N'-(3-fluoro-4-chlorophenyl)urea;
N-(2,6-dichlorobenzoyl)-N'-(4-phenylphenyl)urea;
N-(2,6-dichlorobenzoyl)-N'-(4-cyanophenyl)urea;
N-(2,6-dichlorobenzoyl)-N'-(3-fluoro-4-bromophenyl)urea;
N-(2,6-dichlorobenzoyl)-N'-(3-fluoro-4-iodophenyl)urea;
N-(2,6-dichlorobenzoyl)-N'-(2-fluoro-4-iodophenyl)urea;
N-(2,6-dichlorobenzoyl)-N'-(4-n-propylphenyl)urea;
N-(2,6-dichlorobenzoyl)-N'-(4-trifluoromethylphenyl)urea;
N-(2,6-dichlorobenzoyl)-N'-(3-cyclopropylphenyl)urea;
N-(2,6-dichlorobenzoyl)-N'-(2-methyl-4-chlorophenyl)urea;

N-(2,6-dichlorobenzoyl)-N'-(4-sec-butylphenyl)urea;
N-(2,6-dichlorobenzoyl)-N'-(4-iso-butylphenyl)urea;
N-(2,6-dichlorobenzoyl)-N'-(4-ethylphenyl)urea;
N-(2,6-dichlorobenzoyl)-N'-(4-n-dodecylphenyl)urea;
N-(2,6-dichlorobenzoyl)-N'-(4-benzylphenyl)urea;
N-(2,6-dibromobenzoyl)-N'-(3,4-dichlorophenyl)urea;
N-(2,6-dichlorobenzoyl)-N'-(methyl)-N'-(3,4-dichlorophenyl)urea;
N-(2,6-dichlorobenzoyl)-N'-(ethyl)-N'-(3,4-dichlorophenyl)urea;
N-(2,6-dichlorobenzoyl)-N'-(methyl)-N'-(4-t-butylphenyl)urea;
N-(2,6-dichlorobenzoyl)-N'-(methyl)-N'-(4-bromophenyl)urea;
N-(2,6-dichlorobenzoyl)-N'-(ethyl)-N'-(4-bromophenyl)urea;
N-(2,6-dichlorobenzoyl)-N'-(ethyl)-N'-(4-isopropylphenyl)urea;
N-(2,6-dichlorobenzoyl)-N'-(ethyl)-N'-(4-n-butylphenyl)urea;
N-(2,6-dichlorobenzoyl)-N'-(methyl)-N'-(4-chlorophenyl)urea;
N-(2,6-dichlorobenzoyl)-N'-(ethyl)-N'-(4-chlorophenyl)urea;
N-(2,6-dichlorobenzoyl)-N'-(ethyl)-N'-(4-t-butylphenyl)urea;
N-(2,6-dichlorobenzoyl)-N'-(methyl)-N'-(4-nitrophenyl)urea;
3-(2,6-dichlorobenzoyl)-1-(4-chlorophenyl)-parabanic acid;
N-(2,6-dichlorobenzoyl)-N'-(2,4,5-trichlorophenyl)urea;
N-(2,6-dichlorobenzoyl)-N'-(phenyl)urea;
N-(2,6-dichlorobenzoyl)-N'-(4-nitrophenyl)urea;
N-(2,6-difluorobenzoyl)-N'-(4-trifluoromethylphenyl)urea;
N-(2,6-difluorobenzoyl)-N'-(4-n-butylphenyl)urea;
N-(2,6-difluorobenzoyl)-N'-(4-t-butylphenyl)urea;
N-(2,6-difluorobenzoyl)-N'-(4-isopropylphenyl)urea;
N-(2,6-difluorobenzoyl)-N'-(3-fluoro-4-iodobenzyl)urea;
N-(2,6-difluorobenzoyl)-N'-(3-fluoro-4-chlorophenyl)urea;
N-(2,6-difluorobenzoyl)-N'-(3-trifluoromethylphenyl)urea;
N-(2,6-difluorobenzoyl)-N'-(4-isobutylphenyl)-N'-(methyl)urea;
N-(2,6-difluorobenzoyl)-N'-(4-chlorophenyl)urea;
N-(2,6-difluorobenzoyl)-N'-(4-bromophenyl)urea;
N-(2,6-difluorobenzoyl)-N'-(4-fluorophenyl)urea;
N-(2,6-difluorobenzoyl)-N'-(4-thiomethylphenyl)urea;
N-(2,6-difluorobenzoyl)-N'-(methyl)-N'-(4-chlorophenyl)urea;
N-(2,6-difluorobenzoyl)-N'-(methoxymethyl)-N'-(3,4-dichlorophenyl)urea;
N-((((3-chloro-4-(1,1,2-trifluoro-2-trifluoromethoxy)ethoxy)phenyl)amino)carbonyl)-2,6-difluorobenzamide;
1-[α-(4-chloro-α-cyclopropylbenzylideneaminooxy)-p-tolyl]-3-(2,6-difluorobenzoyl)urea; 1-[3,5-dichloro-4-(3-chloro-5-trifluoromethyl-2-pyridyloxy)phenyl]-3-(2,6-difluorobenzoyl)urea; 1-[4-(2-chloro-α,α,α-trifluoro-p-tolyoxy)-2-fluorophenyl]-3-(2,6-difluorobenzoyl)urea; 1-(3,5-dichloro-2,4-difluorophenyl)-3-(2,6-difluorobenzoyl)urea; 1-(2-chlorobenzoyl)-3-(4-trifluoromethoxyphenyl)urea; 1-[3,5-dichloro-4-(1,1,2,2-tetrafluoroethoxy)phenyl]-3-(2,6-difluorobenzoyl)urea; and N-[2,5-dichloro-4-(1,1,2,3,3,3-hexafluoropropoxy)-phenylaminocarbonyl]-2,6-difluorobenzamide.

6. A method for increasing yield in soybeans by applying, in the absence of insect pressure on the crop comprising treating soybean plants with a composition comprising an inert carrier and an effective amount for increasing seed pod formation, as active ingredient, of a compound of the formula (I):

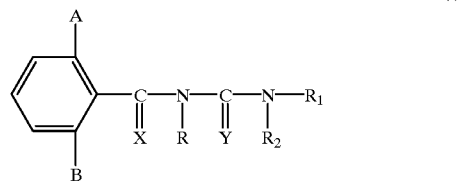

wherein A is a hydrogen atom, a halogen atom, a methyl atom, or a methoxy group;

B also is a hydrogen atom, a halogen atom, a methyl group, or a methoxy group;

R is a hydrogen atom, an alkyl group, a hydroxy group, an alkoxy group, an alkoxymethyl group, an acyl group, or an alkoxycarbonyl group;

X and Y each are an oxygen atom or a sulfur atom;

$R_1$ is a hydrogen atom, an alkyl group that may be substituted with halogen, with alkoxy, with alkylthio, or with cyano, a 1-cycloalkenyl group, a benzyl group that may be substituted with halogen, a hydroxy group, an alkoxy group, an acyl group, an alkoxycarbonyl group, an alkoxythiocarbonyl group, an alkylsulfonyl group, or a phenylsulfonyl group; and $R_2$ is a substituted or non-substituted phenyl group of a pyridyl group that may be substituted with halogen, with nitro, with cyano, or with halogenated alkyl.

7. The method of claim 6, wherein X and Y are the same.

8. The method of claim 6, wherein A is a halogen atom and B is a hydrogen atom.

9. The method of claim 6, wherein A and B are both halogen atoms.

10. The method of claim 6, wherein X and Y are different.

* * * * *

UNITED STATES PATENT AND TRADEMARK OFFICE
CERTIFICATE OF CORRECTION

PATENT NO. : 6,376,430 B1 Page 1 of 1
DATED : April 23, 2002
INVENTOR(S) : R.T. Weiland et al.

It is certified that error appears in the above-identified patent and that said Letters Patent is hereby corrected as shown below:

Column 1,
Line 12, under "BACKGROUND OF INVENTION", please delete "determined" and insert -- determinate -- in its place.

Signed and Sealed this

Sixteenth Day of July, 2002

Attest:

Attesting Officer

JAMES E. ROGAN
Director of the United States Patent and Trademark Office